United States Patent [19]

Croux et al.

[11] Patent Number: 5,354,667
[45] Date of Patent: Oct. 11, 1994

[54] PROCESS FOR THE ENZYMATIC PREPARATION OF 7-AMINOCEPHALOSPORANIC ACID

[75] Inventors: Christian Croux, Madrid; Javier C. Perez, Leon; Jose L. B. Fuentes, Leon; Francisco S. Maldonado, Leon, all of Spain

[73] Assignee: Antibioticos, S.p.A., Milan, Italy

[21] Appl. No.: 740,381

[22] Filed: Aug. 5, 1991

[30] Foreign Application Priority Data

Aug. 3, 1990 [ES] Spain .................................. 9002109

[51] Int. Cl.$^5$ .................... C12P 35/02; C12P 1/19; C12N 1/21; C12N 15/63; C12N 9/80
[52] U.S. Cl. .................. 435/51; 435/252.33; 435/320.1; 435/228; 435/172.3
[58] Field of Search .............. 435/51, 172.1, 172.3, 435/182, 228, 252.1, 252.33, 320.1, 822, 197; 935/59, 73

[56] References Cited

U.S. PATENT DOCUMENTS 4,774,179 9/1988 Ichikawa et al.

FOREIGN PATENT DOCUMENTS 9012110 10/1991 PCT Int'l Appl. ............ C12N 1/16

OTHER PUBLICATIONS

Garcia et al. "An improved method to clone penicilin acylace genes . . . ," J. of Biotech. 3:187–195 (1986).
Forney et al. "Selection of Amidases with Novel Substrate Specificities . . . " Applied and Environ. Microbiology 55(10):2550–2555 (Oct. 1989).
Shibuya et al. "Isolation and Properties of 7β-(4-carboxybutanamido) cephalosporanic Acid Acylase-producing Bacteria," Agric. Biol. Chem. 45(7):1561–7 (1981).
Matsuda et al., "Molecular Cloning and Structure of the Gene for 7β-(4-carboxybutanamido) cephalosporic Acid Acylase from a *Pseudomonas* strain," J. of Bacteriology, 163(3):1222–1228 (Oct. 1985).

*Primary Examiner*—Richard A. Schwartz
*Assistant Examiner*—James Ketter
*Attorney, Agent, or Firm*—Dickstein, Shapiro & Morin

[57] ABSTRACT

A process for the production of an *E. coli* strain producing high yields of 7β-(4-carboxybutanamido) cephalosporin acylase, comprises: (a) digesting the DNA of a microorganism whose DNA includes the sequence encoding 7β-(4-carboxybutanamido) cephalosporin acylase, and forming a plasmidic library; (b) transforming, with the sequences in the plasmidic library, an auxotrophic *E. coli* host; (c) selecting for transformed *E. coli* hosts containing the acylase sequence by growth on a suitable medium; (d) isolating the vector containing the acylase sequence, digesting the vector, and ligating the DNA sequences obtained into an *E. coli* vector under control of an *E. coli* promoter; (e) repeating selection procedure of step (c); (f) using the vectors from the selected *E. coli* hosts to transform an *E. coli* host lacking substantial β-lactamase activity. 7-Aminocephalosporanic acid and its derivatives can be prepared by reaction of substrates like 7β-(4-carboxybutanamido) cephalosporanic acid with 7β-(4-carboxybutanamido) cephalosporin acylase produced by the *E. coli* strain produced by the above process.

6 Claims, No Drawings

PROCESS FOR THE ENZYMATIC PREPARATION OF 7-AMINOCEPHALOSPORANIC ACID

BRIEF DESCRIPTION OF THE SUBJECT MATTER OF THE PATENT

This invention relates to an enzymatic process to prepare 7-aminocephalosporanic acid. More particularly, this invention relates to the description of a method to isolate a gene coding for a 7β-(4-carboxybutanamido)cephalosporin acylase active enzyme through the use of recombinant DNA techniques; the cloning of the said gene in a microorganism of the genus Escherichia; the hyperproduction of said enzyme by fermentation in said microorganism; and the extraction and inmobilization of said enzyme for the enzymatic preparation of 7-aminocephalosporanic acid from 7β-(4carboxybutanamido)cephalosporanic acid.

STATE-OF-THE-ART TECHNOLOGY

For the production of 7β-(4-carboxybutanamido) cephalosporin acylases (hereinafter referred as glutaryl-ACA-acylases) by fermentation, it is known the use of microorganisms such as *Pseudomonas* and *Acinetobacter sp.* (Shibuya et al. (1981) Agr. Biol. Chem. 45, 1561; Matsuda A. et al. (1985) J.Bacteriol. 163, 1222; Matsuda A. et al. (1987) J. Bacteriol. 169, 5815). The production of these enzymes by the above microorganims has several drawbacks. On one hand, the glutaryl-7ACA-acylase activity level is very low, and on the other hand, together with the glutarylacylase activity other enzymes are produced by these microorganisms, such as β-lactamases and acetylases which degrade the 7-aminocephalosporanic acid, with the result of decreasing the production yield and increasing the cost of the final product purification process. In order to avoid such enzymatic contamination, it is required to purify the glutaryl-7ACA-acylase, which increases the cost of and impairs very much the enzymatic process to obtain the 7-aminocephalosporanic acid starting from 7β-(4carboxybutanamido)cephalosporanic acid.

Recently, two processes have been described to isolate the glutaryl-7ACA acylase genes from a *Pseudomonas* GK16 strain (Matsuda A. et al. (1985) J. Bacteriol 163, 1222) and from a *Pseudomonas* SE83 strain (Matsuda A. et al. (1987) J.Bacteriol 169, 5815). In the first process, the gene coding glutaryl-7ACA-acylase was isolated by the individualised assay of the clones obtained from a library of *Pseudomonas* GK16, by an enzymatic assay process. In the second case, the gene coding for glutaryl-7ACA-acylase was isolated by the individualised assay of the clones obtained from a library of *Pseudomonas* SE83, employing an assay microorganism sensitive to the 7-aminocephalosporanic acid, but not to the 7β-(4-carboxybutanamido)cephalosporanic acid. Both procedures are extremely bothersome and ineffective, as they analyse thousands of clones. Moreover, both processes show limitations in sensitivity, especially in the case of the enzymatic method. The glutaryl-7ACA-acylase genes of *Pseudomonas* GK16 and SG83 have been expressed in *Escherichia coli* strains used frequently in genetic engineering (Matsuda A. et al. (1985) J. Bacteriol. 163, 1222, Matsuda A. et al. (1987) J. Bacteriol. 169,, 5815).

The glutaryl-7ACA-acylase-producing *Acinetobacter* sp. isolated from soil, shows extremely low enzymatic yield levels, and it has been necessary to develop extremely tedious mutagenic and screening methods which while improving the production, do not lead to good enough results. With the process of improvement by mutation, a 100–150 times increase has been obtained, which is long way from the 1000 times increase obtained by the present invention. On the other hand, even after screening of better producing mutants, the synthesis of the aforementioned non-desirable enzymes (β-lactamases, esterases, etc.) is not avoided. No reference has been found in the scientific literature regarding the isolation, cloning and identification of the gene coding for the glutaryl 7ACA-acylase from the *Acinetobacter* sp. and its subsequent reinsertion by transformation into *E. coli*.

DESCRIPTION OF THE INVENTION

With the conventional method of random mutation and screening of over-producing strains, it has not been possible to obtain the remarkable increase of the glutaryl-7ACA-acylase activity, possible with the recombinant DNA techniques of the invention. Such yield increase through the recombinant DNA methods bears the additional advantage of excluding the non-desirable enzymatic activities present in the parental strains.

For the purpose of describing this invention, it is possible to start from any microorganism producing glutaryl-7ACA-acylase, such as the *Acinetobacter*, and more specifically from the *Acinetobacter* sp. ATCC 53891 as donor of deoxyribonucleic acid (hereinafter referred to as DNA). Once obtained, its chromosomal DNA (which contains the genetic information encoding the glutaryl-7ACA-acylase), was digested and the resulting DNA fragments inserted in a DNA vector obtained from an *Escherichia coli* strain. The recombinant vectors so obtained were introduced in the cells of a host microorganism not producing glutaryl-7ACA acylase, belonging to the genus *Escherichia* and exhibiting auxotrophy for several compounds. The transformants carrying recombinant vectors expressing glutaryl-7ACA-acylase activity were screened out by the use of an artificial culture medium, in which one or several compounds for which the host is auxotrophic, were substituted by derivatives of said compounds obtained by linkage through an amide type link with the glutaric acid, or with other acids which were or not were derivatives from the glutaric acid, and which are liable to be hydrolysed by the glutaryl-7ACA-acylase produced by the DNA donor strain. For this purpose, the previous verification has to be made by the use of enzymatic extracts coming from the donor strain, that these amide type derivatives for which the glutaryl-7ACA-acylase exhibits an affinity, are hydrolysed by the said enzyme, with the release of glutaric acid and of the compound essential to complement the host auxotrophy and allow its growth, so that the cells able to produce glutaryl-7ACA-acylase could survive in an artificial culture medium as described hereinabove.

Here, it is important to point out that in this artificial culture medium two other cell types could also survive, i.e. the cells having a back-mutation in the gene responsible for the host cell auxotrophy, and the cells having acquired in the recombinant vector the genetic information encoding the enzyme responsible for the auxotrophy in the host cell. To avoid the first type of contaminant cells, there are used host cells exhibiting a very low reversion rate in the mutation controlling the auxotrophy, as for example the cells having lost in whole or in part the gene responsible for the auxotrophy. To avoid the second type of contaminant cells, it is possible to make use of host cells exhibiting two auxotrophies, and to substitute the compounds for which the strain is auxotrophic, by the corresponding glutaryl derivatives, in which case the possibility to find transformants containing at the same time genetic information encoding the two enzymes responsibles for both auxotrophies is extremely low.

Both abovementioned cell types which can appear in the culture plates together with the cells producing glutaryl-7ACA-acylase can be easily differentiated from these last ones because, after some time, around the glutaryl-7ACA-acylase- producing colonies, growing halos of commensal bacteria can be detected which utilize the compound released by the action of the glutaryl-7ACA-acylases. Moreover, the non-producing glutaryl-7ACA-acylase bacteria (having a back-mutation or transformed with genetic information coding for compounds winch complement the auxotrophy) can be differentiated from the glutaryl-7ACA-acylase producing bacteria through a simple plate replication experiment, since the non-producing bacteria may be grown in minimal media in absence of both compound for which auxotrophy is exhibited by them and in absence of its corresponding glutaryl derivative while the producing glutaryl-7ACA-acylase bacteria require both of these two compounds to grow.

Thus according to the present invention a method is provided for the production of an E. coli strain producing high yields of 7β-(4-carboxybutanamido) cephalosporin acylase, comprising:

a) digesting the total DNA of a strain of a microorganism whose DNA includes the sequence encoding 7β-(4-carboxybutanamido) cephalosporin acylase and placing the DNA fragments in a DNA vector so as to form a plasmidic library, b) transforming, with each of the DNA sequences contained in the plasmidic library, an E. coli host that is auxotrophic to a compound capable of forming an amide link with glutaric or a related acid, c) selecting for transformed E. coli hosts containing the sequence encoding 7β-(4-carboxybutanamido) cephalosporin acylase by growth on a medium containing a glutaric acid amide, or a related acid amide, of the compound to which the untransformed E. coli strain is auxotrophic, d) isolating the vector containing the sequence encoding 7β- (4-carboxybutanamido) cephalosporin acylase from the selected host, digesting the vector DNA, and ligating each of the DNA sequences so obtained into an E. coli vector such that it is under the control of an E. coli promoter sequence, e) transforming an E. coli host auxotrophic to a compound capable of forming an amide link with glutaric or a related acid with each of the vectors formed in step (d), and then selecting for transformed hosts containing the sequence encoding 7β-(4-carboxybutanamido) cephalosporin acylase under the control of an E. coli promoter by growth on a medium as in step (c) above, and f) isolating the vectors from the selected E. coli hosts and using them to transform an E. coli host selected to lack substantial β-lactamase activity.

Thus, according to the present invention a method is provided which makes possible to extract the genetic information relative to the glutaryl-7ACA-acylase production of a producing strain and to isolate said genetic information, using as the system to screen out the recombinant vectors a process based on complementing the auxotrophies of a host cell in an artificial medium. The main novelty of this aspect in the present invention lies in the employment of a new direct highly simple screening system which allows to isolate speedily and with a great sensitivity, glutaryl-7ACA-acylase producing clones among a library of recombinant vectors obtained by the use of cloning vectors, with no limitation at all for the system employed, since the screening does not depend on the selection marker present in the vector being a β-lactamase. The new method described herein allows one to analyse complete libraries in one single culture Petri plate, with no need of having the individually available transformants. This means the possibility of, within a short period of time, analysing many different libraries obtained by the use of different vectors and different systems for the DNA digestion. The high sensitivity of the method lies in the fact that the quantities required in general by the bacterium of the compound for which it is auxotrophic can be very small, especially in the case of some vitamins as, for example, the p-aminobenzoic acid. In this case the bacterium can grow even if the activity of the cloned glutaryl-7ACA-acylase is very small, especially if one takes into account that the culture plates may be incubated for several days, allowing time for the production of the quantity of the enzyme required to hydrolyze the glutaryl derivated. A further advantage of such method is that it makes much easier the subcloning work of the glutaryl-7ACA-acylase gene, since by this method the active subcloning may be screened quickly and easily.

The microorganism selected in the specification of this patent as the host for the isolation of the glutaryl-7ACA-acylase gene is the HB101 strain of *Escherichia coli* which exhibits auxotrophy for thiamine, L-proline and L-leucine. Any other strain able to be transformed and auxotrophic for amino-acids or other compounds able to form amide links with glutaric acid or other acids related to the glutaric acid, and able to be hydrolysed by the glutaryl-7ACA-acylases, can also be employed as host cell.

Accordingly, the compound used as a precursor to complement the auxotrophy of the HB101 strain of *Escherichia coli*, was glutaryl-L-leucine. As an example of other compound which has also shown to be useful to isolate the glutaryl-7-ACA-acylase, the succinyl-L-proline may be quoted. Another compound that can also be used is the glutarylamide of the p-aminobenzoic acid, provided that a strain is used which will be auxotrophic for the p-aminobenzoic acid, such as, for example, the strains AB3292 or AB3295 of *Escherichia coli*. As mentioned above, to increase the specificity of the method it is possible to use two compounds at once, such as for example glutaryl-L-leucine and succinyl-L-proline.

Any microorganism producing glutaryl-7 ACA-acylase, and having a gene coding to the compound which can be expressed in the selected host cell, may be used as a source of DNA.

As a DNA donor cell, there may be used for example the glutaryl-7ACA-acylase producing strain *Acinetobacter* sp. ATCC 53891.

The DNA vectors used to describe the isolation process of the glutaryl-7 ACA-acylase gene in *Escherichia coli* HB101 were the plasmids known as pACYC184, pUC18, pBR325. Other plasmids possessing selections markers of resistance to antibiotics may also be used. Depending on the host microorganism employed, other specific DNA vectors, different to those mentioned above, can be used.

In an example of the glutaryl-7ACA-acylase isolation, the first step consists of confirming that the glutaryl-7-ACA-acylase activity of the strain to be used as DNA donor, is able to hydrolyze the glutaryl derivative that will be used subsequently in the selective growth medium. Such verification is made by conventional biochemical techniques. Then, the DNA of the donor of the glutaryl-7ACA-acylase gene is fully or partially digested. The DNA vector—generally a plasmid—is also digested with a restriction endonuclease which at the cutting ends will generate sequences complementary to those of the DNA donor fragments. The vector and the fragments generated in this way are ligated by the use of a ligase-active enzyme such as the T4 DNA ligase. The recombinant vectors resulting from the ligation of the vector with one or more DNA fragments of the donor cell, can be introduced in an appropriate microorganism such as the strain HB101 of *Escherichia coli*, by conventional transformation techniques as, for example, those described in Maniatis T. et al. (1982) Molecular Cloning: A Laboratory Manual, Cold Spring Harbor Laboratory, Cold Spring Harbor, N.Y., U.S.A. The desired transformant is selected in a culture medium in which only those clones possessing the resistance of the DNA vector and bearing the fragment of DNA donor to express the glutaryl-7ACA-acylase activity can be grown, though as it has been indicated hereinbefore, it is possible that other contaminant strains which will have recovered the activity of the gene for which the host cell is auxotrophic will appear in said selective medium. In this case, the glutaryl-7ACA-acylase-producing strains are distinguished because around them a halo of growing satellite commensal bacteria is formed as hereinbefore described. Once the transformant is isolated, confirmation of the expression of the glutaryl-7ACA-acylase can be made, because its cells are able to grow in a medium containing the compound for which the cell is auxotrophic, or the corresponding glutaryl derivative used as a selection compound in the culture medium.

The glutaryl-7ACA-acylase-producing-strain, isolated as described hereinbefore, is then the subject of several microbiological and biochemical tests, to determine the physical map of the recombinant DNA vector, as well as to analyse the enzyme obtained. To be sure the genetic information relative to the glutaryl-7ACA-acylase gene is included in the recombinant vector, it is possible to apply several techniques, e.g. the use of in vitro gene expression systems, maxicells, though it is easier to conduct a simple recloning of the recombinant vector in another host cell different to the host cell used in the isolation and the subsequent verification that the new recombinant strains obtained are also producing glutaryl-7ACA-acylase. The determination of the recombinant vector physical map is drawn by conventional genetic engineering techniques, by the use of several restriction endonucleases. The quantification of the glutaryl-7ACA-acylase is made by conventional spectroqatometric techniques or by the use of HPLC equipment.

Once the physical map of the glutaryl-7ACA-acylase which contains the recombinant vector was drawn, the following step was taken to proceed to the second aspect of the present invention: the hyperproduction of glutaryl-7ACA-acylase in a strain of *Escherichia coli*. For this purpose, the glutaryl-7ACA-acylase-producing transformants were selected by the method described hereinbefore. Thus, it was possible to determine more accurately the location of the glutaryl-7ACA-acylase gene. With the purpose of increasing the transcription level of the glutaryl-7ACA-acylase gene, and in short to increase the production of this enzyme in this microorganism, it was considered possible to place the glutaryl-7ACA-acylase gene under the control of *Escherichia coli* promoter sequences, such as the promoters lac, tac, trc, trp or other promoters conventionally used for the expression of genes in *Escherichia coli*.

To carry out this process, there was selected the recombinant vector containing the glutaryl-7ACA-acylase gene, which had been isolated from the *Acinetobacter* ATCC 53891 genomic DNA, and it was digested with different restriction endonucleases. The fragments resulting thereof were ligated by the use of the enzyme T4 DNA ligase with plasmidic vectors such as for example pBR325, pUC18, pACYC184 or other plasmidic vectors previously digested with restriction endonucleases which had shown restriction sites compatible with the fragments they were to be ligated with. The recombinant vectors so obtained were introduced by transformation in an *Escherichia coli* strain such as *Escherichia coli* HB101, and the transformants producing glutaryl-7ACA-acylase were screened as explained hereinabove. Once the recombinant vectors were obtained, their physical maps were drawn out by means of restriction enzymes, and it was established which DNA fragment contained the glutaryl-7ACA-acylase gene. This fragment of DNA containing the glutaryl-7ACA-acylase gene was inserted in as other plasmidic vector containing a sequence promoter of *Escherichia coli* such as, for example, the plasmid pDR540 which contains the promoter sequence tac (de Boer, H. et al. (1983) Proc. Natl. Acad. Sci. USA 80:21). The glutaryl-7ACA-acylase gene was placed so as to be under the control of the promoter tac. The new recombinant vector so obtained was transformed into an *Escherichia coli* strain such as *Escherichia coli* HB101, and the glutaryl-7ACA-acylase producing transformants were screened out by the method described hereinabove. The production of glutaryl-7-ACA-acylase in these transformants was analysed by evaluating the enzymatic activity present in the extracts obtained from the several transformant cultures. Such evaluation was performed both by spectrofotometric techniques and by HPLC chromatography. In this way, glutaryl-7ACA-acylase-producing strains were obtained, the production levels of which where significantly higher than those from the recombinant *Escherichia coli* strains obtained in the primary isolation specified hereinabove.

The high product yield achieved by this second stage of the process is due to the use of promoter sequences specific for *Escherichia coli* which result in a higher expression to the gene. Since the glutaryl-7ACA-acylase comes from an *Acinetcbacter* sp. and its original promoter sequence has been selected by evolution to work effectively in *Acinetobacter* sp. but not necessarily in *Escherichia coli*, the initial recombinant clones in *E. coli* show low yield levels, since they could be expressing the glutaryl-7ACA-acylase gene through the original promoter. Therefore, the promoter change involves a substantial improvement in the process of this patent.

A third aspect of the process described in this patent consists in the introduction of the recombinant vectors containing the abovementioned glutaryl-7ACA-acylase gene in several strains of *Escherichia coli*, with the purpose of improving the enzyme production levels and the quality of the enzymatic extracts obtained for industrial use, by immobilizing them on several supports. As commented above, most strains usually used to carry out genetic engineering techniques are not appropriate to obtain enzymatic extracts intended for the production of 7-aminocephalosporanic acid, because such strains produce certain quantities of β-lactamases and acetylases which degrade the 7-amino-cephalosporanic acid, and therefore result in a decrease in the final yield.

For the expression of the gene coding for glutaryl-7ACA-acylase in *E. coli*, it is essential that such strain and the plasmids used lack β-lactamase activities which would degrade both the glutaryl-7ACA and the 7-ACA. Many plasmids used for the expression of foreign proteins in *E. coli* have as a selection marker the gene for resistance to ampicillin, which codes for β-lactamase activity. For this reason, all works intended for the expression of genes relative to the biosynthesis of β-lactamic antibiotics are carried out with vectors lacking the ampicillin resistance gene. However, while not being resistant to high ampicillin levels, a great quantity of *E. coli* strains have a basal level of β-lactamase activity. Such is the case of the *E. coli* K12-C-600 used as the microorganism hosting the glutaryl-7ACA-acylase gene (Japan Patent Application # 110292/1985) which possesses a β-lactamase activity that clearly destroys a portion of the substrate. In our invention, we believe it is essential to find strains of *E. coli* not producing β-lactamase, to be used as host for the glutaryl-7ACA-acylase, and in this way the glutaryl-7ACA would be affected only by the activity of glutaryl-7ACA-acylase.

However, we have also found that the strains not producing β-lactamases but hypersensitive to β-lactamase turned out also to be appropriate for the expression of the glutaryl-7ACA-acylase and, consequently, for the improvements producing such enzyme.

To screen out the non β-lactamase producing *E. coli* strains, a colorimetric method has been used to measure such enzymatic activity, based on the employment of the chromogenic cephalosporin "Nitrocefin" (Oxoid). Some of the results obtained are shown in Table I.

TABLE I

| *E. coli* STRAIN | ACTIVITY |
|---|---|
| Control − (with no β-lactamase) | 0 |
| Control + (β-lactamase, Oxoid) | +++++ |
| ATCC 9637 | + |
| ATCC 11105 | + |
| 1070 | + |
| 161 | + |
| 405 (V) | +++++ |
| 498 (P) | ++ |
| M.15 (P) | +++++ |
| M.17 (P) | +++ |
| 7D1D4 | +++++ |
| C1 | +++++ |
| C2 | +++++ |
| B1 | 0 |
| V - 517 | ++ |
| DH 5α | ++ |
| P - 3 (NCIMB 40432) | 0 |
| GP - 1 | +++++ |
| A | 0 |
| K12BM21 | + |
| K12-C-600 | ++ |

Once the *E. coli* strains poor in β-lactamase activity were selected, there were isolated the colonies lacking non desirable enzymatic activities, such as esterase, acetylase, etc. which lead to the appearance of degradation products both from cephalosporin and from 7-ACA.

For this purpose, enzymatic activities were evaluated, by the use as substrate of sodium cephalosporin C in crude extracts of the previous selected strains. Once these strains were selected, the recombinant vector containing the glutaryl-7ACA-acylase previously obtained was inserted in the strain by transformation. The production levels of glutaryl-7ACA-acylase were determinated in the different transformants, and the best producers were selected. The result was the production of glutaryl-7ACA-acylase, non detectable levels of β-lactamases, and reduced levels of 7-aminocephalosporin-acetylases.

The novelty of this third stage of this patent consists in the fact the *Escherichia coli* recombinant strains obtained, not only produce more glutaryl-7ACA-acylase than the parental *Acinetobacter* sp. ATCC 53891 but, furthermore, produce very low levels of enzymes which could degradate the final product 7-aminocephalosporanic acid. The use of the enzymatic extracts resulting from these recombinant microorganisms enable one, with no need to turn to long and expensive purification processes of the glutaryl-7ACA-acylase which increase extremely the cost of the process, to transform 7β-(4-carboxybutanamido) cephalosporanic acid into 7-aminocephalosporanic acid in very high yields.

With the purpose to insert in the *E. coli* strains previously selected the plasmids bearing the gene coding for the glutaryl-7ACA-acylase activity, the first step was to obtain competent cells. As competent cells are designated those cells that by means of a generally chemical treatment show altered the permeability of their membrane, and are able to accept molecules of exogenous DNA. The said plasmids were inserted by transformation in the competent cells.

Transformation means the procedure to introduce the exogenous DNA in the hosting competent cell.

The plasmid introduced, in addition to the glutaryl-7ACA-acylase gene of *Acinetobacter* sp., has selectable marker the gene for resistance to chloramphenicol.

In order to verify the *E. coli* strains resistant to chloramphenicol obtained by transformation were bearing the desired plasmids, there were made minipreparations of plasmidic DNA, from a series of isolated colonies. Later the plasmids were analysed by conventional techniques.

For the production of glutaryl-7ACA-acylase by the use of the previously selected *E. coli*, said *E. coli* are grown in a medium containing a carbon source (e.g., glucose, sucrose, lactose, glycerol, vegetable oils, etc.), a nitrogen source ( e. g., yeast extract, meat extract, soy meal, peanut meal, corn-steep liquor, etc.) and mineral salts. The temperature range for this production is 18°-38° C., and the pH 5-9. For flask fermentation, a 50, 100, 250, 500 ml. and 1 l may be used containing a medium quantity of 10-50% the flask volume. The fermentation lasts for 12-90 hours.

The growing of the recombinant microorganisms can be improved, providing the appropriate conditions to preserve the stability of the recombinant vectors. For example, by the addition to the culture medium of antibiotics such as, for example, chloramphenicol or tetracycline, for which the recombinant vector containing the glutaryl-7ACA-acylase gene shows a resistance marker. This, besides stabilizing the production, avoids the contamination of the culture medium by other undesirable microorganisms and also eliminates the cells which having lost the recombinant vector, have are not able to produce glutaryl-7ACA-acylase.

The glutaryl-7ACA-acylase produced in the recombinant micro-organism may be recovered by centrifuging the culture medium, in order to separate the cells and to immobilize them by conventional procedures. The immobilized *E. coli* cells may be used to transform solutions of glutaryl-7ACA in 7-ACA, at the acting pH and temperatures of the enzyme (pH 6.5, 8.5; 20°–40° C). The 7-ACA obtained is also separated by conventional procedures.

The glutaryl-7ACA acylase can also be purified from the enzymatic extract. For that, once the *E. coli* cells have been centrifuged, they are broken up by conventional methods (pressure, sonication, osmotic shock, etc.), and the extract obtained is purified by conventional precipitation, chromatographic, and membrane techniques.

The concentrated enzymatic extracts are then immobilized reacting them with the appropriate inert supports (e.g., Eupergit R): the immobilized enzyme is cyclically used for the transformation of glutaryl-7ACA solutions and for 7-ACA isolation by known techniques. The invention will be illustrated next by the following Examples:

EXAMPLE 1

1. Assay of the ability of the glutaryl-7ACA-acylase produced by the Acinetobacter ATCC 53891 to degradate the glutaryl-L-leucine.

One 0.1 ml aliquot of a purified glutaryl-7ACA-acylase preparation proceeding from the *Acinetobacter* sp. ATCC 53891 strain, showing an activity of 3 U/l. (1 U is equivalent to the quantity of enzyme required to release 1 $\mu$mol of 7-amino-cephalosporanic acid in 1 minute, at 37° C.) was incubated with a 0.1 ml aliquot of a 10 mg/ml solution of glutaryl-L-leucine, in the presence of 100 mM phosphate buffer at pH 8.0 for 10 hours at 37° C. The presence of L-leucine in this mixture was shown both by the staining of the reaction with the addition of ninhydrine to the mixture, and by the analysis of the reaction products in an amine acid analyser. Thus, there was demonstrated that the glutaryl-7ACA-acylase is able to hydrolyse the glutaryl-L-leucine.

2. Preparation of the DNA vector

The plasmid vectors pACYC184 (Tot$^r$, Cam$^r$), pUC18 (Amp$^r$) and pDR540 (Amp$^r$) containing resistance markers for several antibiotics, were prepared as follows: The strains of *Escherichia coli* individually possessing the abovementioned plasmids, were incubated for 16 hours at 37° C. in 0.5 l of a medium that containing 10 g/l. yeast extract; 5 g/l. NaCl;. After incubation the cells were settled, washed, lysated, and the plasmids were isolated by the alkaline method (Maniatis T. et al. (1982) Molecular Cloning: A Laboratory Manual, Cold Spring Harbor Laboratory, Cold Spring Harbor, N.Y., USA). The DNA obtained by this method was purified by centrifugation in CsCl gradient.

3. Preparation of the DNA donor incorporating the genetic information relative to glutaryl-7ACA-acylase production.

The strain of *Acinetobacter* sp. ATCC 53891 was grown in a medium containing (in g/l): acid sodium glutamate, 5; KH2PO4, 1,5; collagen hydrolysate, 25; corn-steep liquor, 5; and glucose, 2. The incubation lasted 48 hours at 25° C. temperature. Then, the cells were settled, washed and lysated with SDS 1%, EDTA 20 mM and proteinase K 0.1 mg/ml. The lysis mixture was heated at 55° C. for 3 hours. Next, the mixture was extracted several times with phenol and chloroform-isoamylic alcohol, and the aqueous phase containing the DNA was precipitated with ethanol. The DNA precipitated was washed with ethanol 100% and ethanol 70%, and dissolved in 10 mM Tris-HCl buffer, pH 7.5 which contained EDTA 1 mM.

4. Insertion of the DNA donor fragments in the DNA vectors

Several samples containing 1 $\mu$g. of the DNA obtained from the *Acinetobacter* sp. ATCC 53891 strain were digested with the restriction endonuclease BamHI at 37° C., and at different times the reactions were stopped by heating the sample at 65° C. for 10 minutes. In this way, several partial DNA digestions were obtained, which were displayed by staining them with ethidium bromide following their electrophoresis in agarose gels.

Several samples containing 2 $\mu$g DNA from the pA-CYC184 plasmid were digested with the restriction endonuclease BamHI at 37° C. for 1 hour, and were heated at 65° C. for 10 minutes to stop the reaction.

Each sample from the DNA partial BamHI digestions of the *Acinetobacter* sp. was ligated with a sample of the plasmid pACY184 *BamHI* digestion by the T4 DNA ligase in the presence of ATP, Mg$^{2+}$ ions and 2-mercaptoethanol for 16 hours at 14° C.

By this process, several recombinant vectors collections containing DNA fragments of *Acinetobacter* sp. ATCC 53891 inserted in the plasmid pACYC184 were obtained.

5. Genetic transformation of a host cell with recombinant vectors and isolation of the glutaryl-7ACA-acylase gene.

The host cell selected for the transformation was the *Escherichia coli* HB101 strain. To make these cells competent, there was used the RbCl method described in Maniatis T. et al. (1982), Molecular Cloning: A Laboratory Manual, Cold Spring Harbor Laboratory, Cold Spring Harbor, N.Y., York, U.S.A. Different aliquots of competent *Escherichia coli* HB101 cells were mixed with the different aliquots of the recombinant vector collections obtained in the stage (4).

The mixtures of competent cells and recombinant vectors were incubated for 15 minutes at 4° C., and next they were heated at 37° C. for 3 minutes. Then, 1 ml aliquots of the LB medium were added to the above aliquot and were incubated for 1 hour at 37° C. The cells were settled and washed with a solution of 8.5 g/l NaCl. Then, these cells were seeded in Petri plates containing M9 saline medium (Maniatis, T.. et al. (1982) Molecular Cloning, A Laboratory Manual, Cold Spring Harbor Laboratory, Cold Spring Harbor, N.Y., USA), 2 g/l glucose; 1 mg/l thiamine-HCl; 100 mg/l L-proline; 50 mg/l chloramphenicol; 5 mg/l glutaryl-L-leucine; and 1.5 g/l agar. The plates were incubated at 37° C. and within 4–7 days the colonies were collected and isolated.

Around the colonies able to produce glutaryl-7ACA-acylase, a growth halo of satellite colonies was observed. The glutaryl-7ACA-acylase-producing colonies are distinguished from the bacteria reverting for the gene leuB, or from the bacteria with a gene incorporated equivalent to the leuB gene of the *Escherichia coli* HB101 strain, because in addition to form growth halos around them, they are capable to grow only in Petri plates containing an artificial medium such as the medium described hereinbefore, which contains L-leucine or glutaryl-L-leucine. Here, it has to be stressed that when to the abovementioned culture in the Petri plates there was added L-leucine, and the L-proline was substituted by for succinyl-L-proline, the cells having the ability to produce glutaryl-7ACA-acylase were capable to grow while the other cells had not such ability. This results from the fact the glutaryl-7ACA-acylase is also capable to hydrolyse the succinyl-L-proline, to release the L-proline essential for the growing of the *Escherichia coli* HB101 bacterium.

In this way, there was obtained the *Escherichia coli* HB101 (pJCll) strain bearing a recombinant plasmid derived from pACYC184 containing a DNA insert of *Acinetobacter* sp. ATCC 53891 in the BamH1 site, of about 8.5 Kb, and which confers on the bacterium the ability to produce glutaryl-7ACA-acylase. This plasmid confers also on this bacterium the resistance to chloramphenicol.

The *Escherichia coli* HB101 (pJC11) strain was grown in LB medium for 20 hours, at 37° C. Next, the glutaryl-7ACA-acylase was released from inside the cells by sonication. The enzymatic activity was determined by a conventional colorimetric method (Balashingham K. et al. (1972) Biochem. Biophys. Acta 276, 250) in which the calibrated curve was calculated by using 7-aminocephalosporanic acid as standard. The glutaryl-7ACA-acylase activity determined was 0.02 U/rag protein. These values were also calculated by using a HLPC chromatography, with the obtention of the same results.

6. Subcloning of the glutaryl-7ACA-acylase gene in expression vectors

Several samples of the pJCll plasmid were digested with the restriction endonuclease EcoRV for 1 hour at 37° C., and then a digestion was carried out with the restriction endonuclease HincII at 37° C., the reaction being stoped at different time intervals by heating the samples at 65° C. for 10 minutes. Thereby, a complete digestion is obtained of the plasmid with the enzyme EcoRV, and a partial digestion with the enzyme HincII.

Furthermore, several samples containing 1 μg of the plasmid pUC18 were digested with the restriction endonuclease HincII for 1 hour at 37° C., and were heated 65° C. for 10 minutes, for stopping the reaction.

Each sample of the plasmid pJCII digestion was joined together with a sample of the plasmid pUC18 digestion, and were ligated with T4 DNA ligase, and the several ligation mixtures were used to transform competent *Escherichia coli* HB101 cells by the same process described in paragraph ( 5). The glutaryl-7ACA-acylase-producing strains were isolated by their growth in Petri plates which contained an artificial selective culture medium, similar to that described in paragraph (5), except for the chloramphenicol that was substituted for 100 rag/1. ampicillin.

So, there was obtained the *Escherichia coli* HB101 (pJC40) strain which in the HincII site of the plasmid pUC18 contains a DNA insert of about 3 Kb containing the glutaryl-7ACA acylase gene of the *Acinetobacter* sp. ATCC 53891.

Several samples containing 1 microgram of the plasmid pJC40 were digested with the restriction nuclease BamH1 at 37° C., and were heated at 65° C. for 10 minutes to stop the reaction. The commercial plasmid pDR540 (Pharmacia-LKB Fine Chemicals) contains the promoter tac close the BamH1 site, and thereby it is possible that the genes inserted in such site may express themselves through such promoter.

Each sample of the plasmid pJC40 digestion was joined together a with a sample of the plasmid pDR540 digestion, and was ligated with T4 DNA ligase and the ligation mixtures were used to transform competent *Escherichia coli* HB101 cells by the same process described in paragraph (5).

The glutaryl-7ACA-acylase were isolated by growing them in Petri plates containing a selective artificial culture medium similar to the medium described for the isolation of the pJC40. The bacteria expressing the glutaryl-7ACA-acylase gene by means of the promoter tac were distinguishable from the bacteria containing the plasmid pJC40 because the former, by expressing better the glutaryl-7ACA-acylase grew at a higher rate, and therefore produced larger colonies in the selection plates.

Thus, the *Escherichia coli* HB101 (pJC40 11) strain was isolated which in the BamH1 site of the plasmid pDR540 contains a DNA insert of approximately 2.8 Kb which contains the glutaryl 7-ACA-acylase gene of the *Acinetobacter sp. ATCC* 53891.

Since the plasmid pJC540 11 confers resistance to ampicillin, because it expresses a β-lactamase which would degrade the 7-aminocephalosporanic acid, it was necessary to shift the fusion of the promoter tac and the glutaryl-7ACA-acylase gene into a different plasmid not conferring resistance to the β-lactamic antibiotics. For that, 1 μg. of the plasmid pJC40 11 was digested with the restriction endonucleases Xbal and HindIll at 37° C. for 1 hour, and the same was done with 1 microgram of the plasmid pACYC184, both reactions being inactivated at 65° C. for 10 minutes. Both digestions were put together and ligated with T4 DNA ligase, using the ligation mixture to transform competent cells of *Escherichia coli* HB101, as described in paragraph (5). The glutaryl-7ACA-acylase producers were isolated by growing them in Petri plates containing a selective artificial culture medium, similar to the culture medium described for the isolation of the pJC11.

In this way, there was isolated the *Escherichia coli* HB101 (pJC200) strain which, between the HindIII and the XbaI sites of the plasmid pACYC184 contains a DNA insert of approx. 2.9 Kb containing the glutaryl-7ACA-acylase gene of the *Acinetobacter* sp. ATCC 53891 fused with the promoter tac.

The *Escherichia coli* HB101 (pJC200) was grown in LB medium for 20 hours, at 37° C. Next, the cells were settled, and the glutaryl-7ACA-acylase was released from inside the cells by sonication. The enzymatic activity was evaluated by the method described in paragraph (5). The determined glutaryl-7-ACA-acylase activity was 0,2 U/mg protein.

7. Introduction of the plasmid pJC200 in different *Escherichia coli* strains

In spite of having achieved a production improvement with the plasmid pJC200, the *Escherichia coli* HB101 strain containing such plasmid was not considered appropriate to produce glutaryl-7ACA-acylase, because in the enzymatic extracts of these cells there were detected enzymatic activities that partially degraded the 7-aminocephalosporanic acid, the final product from the glutaryl-7-ACA-acylase reaction. That is why several *Escherichia coli* strains from our own collection were transformed, by making them competent by a method similar to the method described in paragraph (5).

As a result of these works, the *Escherichia coli* P-3 (pJC200) strain was isolated. *Escherichia coli* strain P-3(pJC-200) was deposited Jul. 22, 1991 with an International Depository authority (NCIMB Ltd., 23 St. Machar Drive, Aberdeen, Scotland, U.K., AB2 1RY) pursuant to the Budapest Treaty Under Accession No. NCIMB 40433 This *Escherichia coli* P-3 (pJC200) strain was grown in TB medium for 48 hours, at 21° C. Then, the cells were settled, and the glutaryl-7ACA-acylase was released from inside the cells by sonication. The enzymatic activity was evaluated by the colorimetric method described in paragraph (5). The determined glutaryl-7ACA-acylase activity was 2 U/mg protein. These values were also calculated by a HPLC chromatography method, with the same results being obtained.

The increase in the glutaryl-7ACA-acylase yield by means of the *Escherichia coli* P-3 (pJC200) strain is quite higher both than the original strain of *Acinetobacter* sp. ATCC 53891 and than any other recombinant strain obtained previously. Furthermore, the extracts of these new glutaryl-7ACA-acylase producing recombinant strains do not contain detectable enzymatic activities which would degrade the 7-aminocephalosporanic acid, and therefore, they are very useful as a source of glutaryl-7ACA-acylase, for being immobilized in supports for industrial use.

EXAMPLE 2

To verify the esterasic activity of the strains, there were obtained cellular extracts resulting from equivalent quantities of cellular paste. The said extracts were mixed with a 1:1 solution of cephalosporin C in phosphate buffer 0,1 M, pH: 7, such as the reaction mix will contain 5000 U/ml cef. C.

The rate of desacetyl Cef. C. appearance against the original Cef. C is, after 8 hour of incubation at room temperature:

|  | % Desacetyl Cef. C. |
| --- | --- |
| Control (Cef. C) | 1.8 |
| *E. coli* A (pJC200) | 49.7 |
| *E. coli* P-3 (pJC200) | 87 |

EXAMPLE 3

This example relates to the obtention of a *E. coli* P-3 strain, transformed by the plasmid pJC200 carrying the gene producing the glutaryl-7ACA-enzyme, and having chloramphenicol resistance marker.

A. In order to obtain competent cells of *E. coli* (liable to be transformed with the desired plasmid), the following steps are taken:

250 ml. flasks with 50 ml. SOB medium (Hanahan, D. (1983) J. Mol. Biol. 166, 557) are seeded with *E. coli* P-3 cells (*E. coli* strain P-3 was deposited Jul. 16, 1991 with an International Depository Authority (NCIMB Ltd., 23 St. Machar Drive, Aberdeen, Scotland, U.K., AB2 1RY) pursuant to the Budapest Treaty under Accession No. NCIMB 40432), and are incubated for 15–18 hours at 37° C. and 250 r.p.m. 500 ml flasks with 50 ml SOB medium are inoculated with 100 μl of previous culture, are grown at 37° C. and 250 r.p.m., up to get an OD$_{600}$=0.4, the cells are collected by centrifugation at 2500 r.p.m. in a top-desk centrifuge, at 4° C., and resuspended in ⅓ of the initial volume of RF1 (Hanahan, D. (1983) J. Biol. 166, 557). This suspension is incubated on ice for 15 min, centrifuged again under the conditions described hereinabove, and resuspended in 1/12 of the initial cultive volume of RF2 (Hanahan, D. (1983) J.Mol. Biol. 166, 557)

The competent cells so obtained are incubated on ice for 15 min. and are distributed in 400 μl aliquot, which are instantaneously frozen in a dry ice-ethanol bath.

B. The transformation of these competent cells with the plasmid pJC200 is carried out through the following steps:

The cells obtained in the point A are slowly thawed out, and immediately 100 μl of the said cells are mixed with 10–15 μg plasmid. The mixture is incubated on ice for 30 min. Next, the mixture is subject to thermal shock for 45 sec. at 42° C., and is immediately incubated on ice for 2–5 min. 1 ml SOB is added, and incubation is performed at 7° C. for 1 hour under gentle shaking (about 100 r.p.m. ). The cells transformed are seeded in LB medium plates with chloramphenicol (30 μg/ml), and is incubated at 37° C. for 15–18 hours.

| C. - Biochemical and growth characteristics of the *E. coli* P-3 pJC200 cells obtained by this process. | |
| --- | --- |
| Growth, 30–37° C. | + |
| Facultative anaerobe | + |
| TSI (triple sugar iron) | A/A |
| ONPG (β-galactosidase) | + |
| ADH (arginindihydrolase) | − |
| LDC (lysine decarboxilase) | + |
| ODC (ornithine decarboxylase) | + |
| Citrate use | − |
| Malonate use | − |
| SH$_2$ production | − |
| Urease | − |
| Indole production | + |
| Acetoin production | − |
| Acetamide hydrolysis | − |
| Esculin hydrolysis | − |
| Indoxyl-beta-D-glycoside | − |
| Gelatin hydrolysis | − |
| Sugars fermentation: | |
| Glucose | + (slow) |
| Raffinose | + |
| Sorbitol | + |
| Succrose | + |
| Inositol | − |
| Adonitol | − |
| Rhamnose | + |
| L-arabinose | + |
| Oxidation of sugars with acid production. | |
| Glucose | + |
| Mannitol | + |
| Inositol | − |
| Sorbitol | + |
| Rhamnose | + |
| Maltose | + |
| Xylose | + |
| Sucrose | + |
| Melobiose | + |
| Amygdalin | − |
| Arabinose | + |
| Growth in the presence of DP-300 (30 μg/100 ml) | − |
| Growth in the presence of DP-300 (30 μg/100 ml) | − |
| Growth in the presence of p-cumaric acid (2 mg/ml) | + |
| Growth in levine agar | + |
| Grow in Mac Conkey agar | + |

EXAMPLE 4

This example relate to the growing of the transformed *E. coli* P-3 (pJC200) strain, obtained as described in Example 1 for the production of the glutaryl-7ACA-acylase enzyme.

A slant of LA medium (composition in g/l: bactotryptone, 10; bacto-yeast extract, 5; NaCl, 10; chloramphenicol, 0.03; agar, 15) seeded from a frozen vial of the said strain is suspended in 5 ml. of 0, 9% sterile saline solution.

An inoculum of TB liquid medium (composition in g/l: bactotryptone, 12; yeast extract, 24; glycerol, 4; $KH_2PO_4$, 2.31; $K_2HPO_4$, 12.54; chloramphenicol, 0.03) was seeded with 0,5 ml of the suspension in a 500/100 ml flask, and was then incubated at 28° C. and 250 r.p.m. for 24 h.

A 500/100 flask, with the same medium is seeded with the previous one (1% seed) and incubated at 21° C. and 250 r.p.m. for 48–72 h.

The cells were separated from the broth by centrifugation at 4000 r.p.m. for 20 min., and then resuspended in phosphate buffer 0,1M, pH 8.0 up to the initial broth volume.

This cells suspension was titrated colorimetrically or by HPLC.

By this process there was obtained a 400 times increase of the enzymatic activity, compared with the original *Acinetobacter* sp. ATCC 53891 strain.

EXAMPLE 5

This example refers to the growing of the transformed *E. coli* P-3 (pJC200) strain aimed to the obtention of the glutaryl-7ACA-acylase enzyme with a new fermentation medium.

An inoculum was prepared as described in Example 4.

The said inoculum was 1% reseeded in a 500 ml. flask containing the medium of the following composition in g/l: yeast autolysate, 24, casein hydrolysate, 12 glycerol, 4; $PO_4H_2K$, 2.314; $PO_4HK_2$, 12.54, following the sterilisation, a solution of chloramphenicol was added for final concentration of 30 μg/ml, afterwards an incubation was made at 21° C. and 250 r.p.m. for 48–72 h.

The cells were separated from the broth by centrifugation at 4.000 r.p.m., for 20 min., and resuspended in phosphate buffer 0,1M, pH 8.0, up to the initial broth volume.

The above cells suspension was titrated by the colorimetric method or by HPLC.

By this process, a 500 times increase of the enzymatic activity was obtained, compared with the *Acinetobacter* sp. ATCC 53891 strain.

EXAMPLE 6

In this example, there are described the growing conditions and the productions obtained with the *E. coli* A(pJC200) strain.

The specifications in Example 4 for the preparation of the culture broth and the separation of cells, were applied to a frozen vial of the *E. coli* A (pJC200) strain.

The production of glutaryl-7ACA-acylase obtained in this case was 600 times higher than the productions obtained from the *Acinetobacter* sp. ATCC 53891 strain.

EXAMPLE 7

Activity of the broth with whole cells 1.5 l of culture medium, prepared as described in Example 5 modified by the addition of 0,4% glycerol at 24 and 48 h., with $O.D._{600}=22$, were centrifuged at 5000 g and thereby there were obtained 85 g of cellular paste (humidity, 80%).

1 g of the cellular paste so obtained was suspended in 50 ml. of phosphate buffer 0,1M, pH 8,0, containing 2% glutaryl-7ACA, and incubated for 10 min. at 37° C. After such period of time, the reaction was stopped by the addition of 20% acetic acid, at the rate of 3 ml for 1 ml of the reaction mixture. The suspension obtained was centrifuged and the 7-ACA formed was quantified in the clear supernatant.

The control performed by HPLC against a standard of 7-ACA showed an activity in the starting broth which represents 1000 times increase compared with the *Acinetobacter* sp. ATCC 53891 strain.

EXAMPLE 8

Activity of the broth with lysate cells 10 g of cells obtained as described in Example 4 were suspended in 50 ml. phosphate buffer 0,1 M, pH 8,0 and subject to an ultrasonic rupture (5 pulses 15 sec. each).

40 ml cellular homogenate were obtained that retains 91% of the activity, before the cellular rupture (measured by HPLC).

We claim:

1. A process for the production of high yields of 7-aminocephalosporanic acid comprising:
  a) digesting the total DNA of a strain of *Acinetobacter* which is deposited under ATCC 53891 whose DNA includes the sequence encoding 7-beta-(4-carboxybutanamido) cephalosporin acylase and placing the resultant DNA fragments in DNA vectors so as to form a plasmidic library,
  b) transforming, with each of the resultant DNA sequences contained in the plasmidic library, a *E. coli* host cells that are auxotrophic to leucine,
  c) selecting for a transformed *E. coli* cell containing the sequence encoding 7-beta-(4-carborybutanamido) cephalosporin acylase by growth on a medium containing the glutaric acid amide of leucine,
  d) isolating the vector containing the sequence encoding 7-beta-(4-carboxybutanamido) cephalosporin acylase from the resultant selected cell, digesting the vector DNA, and figuring each of the DNA sequences so obtained into an *E. coli* vector such that each of said DNA sequence is under the transcriptional control of *E. coli* tac promoter sequence,
  e) transforming an *E. coli* host auxotrophic to leucine with each of the vectors formed in step (d), and then selecting for transformed hosts containing the sequence encoding 7; -beta-(4-carboxybutanamido) cephalosporin acylase under the transcriptional control of the *E. coil tac* promoter by growth on a medium as in step (c) above,
  f) isolating the vectors from the resultant selected *E. coli* cells and using said vectors to transform an *E. coli* host deposited under NCIMB 40432 which is selected to lack substantial beta-lactamase activity,
  g) culturing the resultant transformed *E. coli* under conditions which enable expression of 7-beta-(4-carboxybutanamido) cephalosporin acylase, recovering the resultant expressed 7-beta-(4-carboxybutanamido) cephalosporin acylase from whole broth, and
  h) reacting in an aqueous medium of 7-beta-(4-carboxybutanamido) cephalosporanic acid or a salt thereof with said 7-beta-(4-carboxybutanamido)

cephalosporin acylase recovered from said whole broth to produce said 7-aminocephalosporanic acid.

2. A process for the production of an *E. coli* strain, producing high yields of 7-beta- (4-carboxybutanamido) cephalosporin acylase, comprising:
   a) digesting the total DNA of a strain of *Acinetobacter* which is deposited under ATCC 53891 whose DNA includes the sequence encoding 7-beta-(4-carboxybutanamido) cephalosporin acylase and placing the resultant DNA fragments in a DNA vector so as to form a plasmidic library,
   b) transforming, with each of the resultant DNA sequences contained in the plasmidic library, *E. coli* host cells that are auxotrophic to leucine,
   c) selecting for a transformed *E. coli* cell containing the sequence encoding 7-beta-(4-carboxybutanamido) cephalosporin acylase by growth on a medium containing the glutaric acid amide of leucine,
   d) isolating the vector containing the sequence encoding 7-beta- (4-carboxybutanamido) cephalosporin acylase from the resultant selected cell, digesting the vector DNA, and ligating each of the DNA sequences so obtained into an *E. coli* vector such that each of said DNA sequences is under the transcriptional control of *E. coli tac* promoter sequence,
   e) transforming an *E. coli* host auxotrophic to leucine with each of the vectors formed in step (d), and then selecting for transformed hosts containing the sequence encoding 7-beta- (4-carboxybutanamido) cephalosporin acylase under the transcriptional control of the *E. coli tac* promoter by growth on a medium as in step (c) above, and
   f) isolating the vectors from the resultant selected *E. coli* cells and using said vectors to transform an *E. coli* host deposited under NCIMB 40432 which is selected to lack substantial β-lactamase activity.

3. A process for the production of high yields of 7-beta-(4-carboxybutanamido) cephalosporin acylase comprising:
   a) digesting the total DNA of a strain of *Acinetobacter* which is deposited under ATCC 5:3891 whose DNA includes the sequence encoding 7-beta-(4-carboxybutanamido) cephalosporin acylase and placing the resultant DNA fragments in DNA vectors so as to form a plasmidic library,
   b) transforming, with each of the resultant DNA sequences contained in the plasmidic library, a *E. coli* host cells that an auxotrophic to leucine,
   c) selecting for a transformed *E. coli* cell containing the sequence encoding 7-beta-(4-carboxybutanamido) cephalosporin acylase by growth on a medium containing the glutaric acid amide of leucine,
   d) isolating the vector containing the sequence encoding 7-beta-(4-carboxybutanamido) cephalosporin acylase from the resultant selected cell, digesting the vector DNA, and ligating each of the DNA sequences so obtained into an *E. coli* vector such that each of said DNA sequence is under the transcriptional control of *E. coli tac* promoter sequence,
   e) transforming an *E. coli* host auxotrophic to leucine with each of the vectors formed in step (d), and then selecting for transformed hosts containing the sequence encoding 7-beta-(4-carboxybutanamido) cephalosporin acylase under the transcriptional control of the *E. coli tac* promoter by growth on a medium as in step (c) above,
   f) isolating the vectors from the resultant selected *E. coli* hosts and using said sectors to transform an *E. coli* host deposited under NCIMB 40432 which is selected to lack substantial beta-lactase activity, and
   g) culturing the resultant transformed *E. coli* under conditions which enable expression of 7-beta-(4-carboxybutanamido) cephalosporin acylase, and recovering said 7-beta-(4-carboxybutanamido) cephalosporin acylase from whole broth.

4. A strain of *E. coli* deposited under NCIMB 40433, or progeny thereof capable of producing high yields of 7β-(4-carboxybutanamido) cephalosporin acylase.

5. The pJC200 plasmid containing a DNA sequence encoding 7-beta- (4-carboxybutanamido) cephalosporin acylase under the transcriptional control of *E. coli tac* promoter sequence which is the plasmid in the *E. coli* strain of claim 4.

6. The pJC200 plasmid containing a DNA sequence encoding 7-beta-(4-carboxybutanamido) cephalosporin acylase under the control of the *E. coli tac* promoter sequence.

* * * * *